(12) United States Patent  
Riechers et al.

(10) Patent No.: US 9,199,928 B2
(45) Date of Patent: Dec. 1, 2015

(54) FLUORESCENT DYE FOR PH SENSOR (75) Inventors: Daniel Riechers, Regensburg (DE);
Eberhard Wuenn, Goettingen (DE)

(73) Assignee: SARTORIUS STEDIM BIOTECH GMBH (DE)

( * ) Notice: Subject to any disclaimer, the term of this patent is extended or adjusted under 35 U.S.C. 154(b) by 197 days.

(21) Appl. No.: 14/115,191

(22) PCT Filed: Mar. 28, 2012

(86) PCT No.: PCT/EP2012/001345
§ 371 (c)(1),
(2), (4) Date: Nov. 1, 2013

(87) PCT Pub. No.: WO2012/152355
PCT Pub. Date: Nov. 15, 2012

(65) Prior Publication Data
US 2014/0080222 A1  Mar. 20, 2014

(30) Foreign Application Priority Data
May 11, 2011 (DE) .......................... 10 2011 101 207

(51) Int. Cl.
*G01N 31/16* (2006.01)
*C07C 311/29* (2006.01)
(Continued)

(52) U.S. Cl.
CPC .............. *C07C 311/29* (2013.01); *C09B 3/18* (2013.01); *C09K 11/06* (2013.01); *G01N 21/643* (2013.01);
(Continued)

(58) Field of Classification Search
None
See application file for complete search history.

(56) References Cited

U.S. PATENT DOCUMENTS 2,094,224 A   9/1937  Tietze et al.
4,798,738 A   1/1989  Yafuso et al.
(Continued)

FOREIGN PATENT DOCUMENTS

AT   385 755      5/1988
DE   196 81 363   7/2002
(Continued)

OTHER PUBLICATIONS

Gonzalez-Benito et al., "Fluoresence-Labeled Pyrenesulfonamide Response for Characterizing Polymeric Interfaces in Composite Materials"—Journal of Fluorescence, vol. 10, No. 2, 2000—pp. 141-146.

(Continued)

*Primary Examiner* — Robert Xu
(74) *Attorney, Agent, or Firm* — Gerald E. Hespos; Michael J. Porco; Matthew T. Hespos

(57) ABSTRACT

The present invention relates to a new type of fluorescent with the following formula (I), its preparation process, and also an optical pH sensor which comprises this fluorescent dye immobilized on an analyte-permeable carrier.

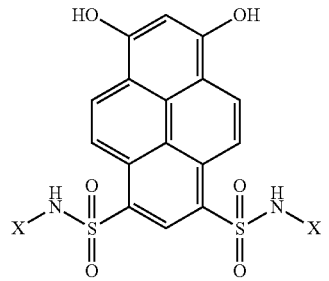

formula (I)

14 Claims, 9 Drawing Sheets

(51) Int. Cl.
*C09K 11/06* (2006.01)
*G01N 21/64* (2006.01)
*G01N 21/80* (2006.01)
*C09B 3/18* (2006.01)

(52) U.S. Cl.
CPC ............ *G01N 21/6428* (2013.01); *G01N 21/80* (2013.01); *C07C 2103/50* (2013.01); *C09K 2211/1011* (2013.01)

(56) References Cited

U.S. PATENT DOCUMENTS

| | | |
|---|---|---|
| 4,844,841 A | 7/1989 | Koller et al. |
| 4,945,171 A | 7/1990 | Haugland et al. |
| 5,273,716 A | 12/1993 | Northrup et al. |
| 5,567,624 A | 10/1996 | Smith |
| 5,569,366 A | 10/1996 | Chen et al. |
| 6,312,644 B1 | 11/2001 | Moriarty et al. |
| 6,949,632 B2 | 9/2005 | Conrad et al. |
| 7,390,462 B2 | 6/2008 | Rao et al. |
| 7,608,460 B2 | 10/2009 | Reed et al. |
| 7,824,918 B2 | 11/2010 | Suri |
| 2003/0049714 A1 | 3/2003 | Conrad et al. |
| 2006/0083688 A1 | 4/2006 | Singaram et al. |
| 2008/0261235 A1 | 10/2008 | Bhatt et al. |
| 2009/0149656 A1 | 6/2009 | Singaram et al. |
| 2010/0068748 A1 | 3/2010 | Gee et al. |
| 2010/0178664 A1 | 7/2010 | Bickmeyer et al. |
| 2010/0274110 A1 | 10/2010 | Markle et al. |

FOREIGN PATENT DOCUMENTS

| | | | | |
|---|---|---|---|---|
| DE | 101 52 994 | | 8/2003 | |
| DE | 10 2007 034 886 | | 12/2008 | |
| DE | 10 2008 040 513 | | 1/2010 | |
| WO | WO 90/05916 | * | 5/1990 | ........... G01N 33/533 |
| WO | 00/01663 | | 1/2000 | |
| WO | 2004/027388 | | 4/2004 | |
| WO | 2008/097747 | | 8/2008 | |
| WO | 2008/157382 | | 12/2008 | |
| WO | 2009/078970 | | 6/2009 | |
| WO | 2010/116142 | | 10/2010 | |

OTHER PUBLICATIONS

Gonzalez-Benito et al., "Pyrene-Doped Polyorganosiloxane Layers over Commercial Glass Fibers"—Journal of Fluorescence, vol. 9, No. 1, 1999—pp. 51-57.
International Search Report of Jun. 22, 2012.
German Office Action of Sep. 8, 2011.

* cited by examiner

M medium to be analyzed
SP sensor patch
F optical window
RW reactor wall
LWL light guide
BP bandpass filter
DS dichroic mirror
LED light-emitting diode
PD photodiode
DSP digital signal processor (lock-in amplifier)

FLUORESCENT DYE FOR PH SENSOR

BACKGROUND

1. Field of the Invention

The present invention relates to a new type of fluorescent dye, to its preparation process, and to an optical pH sensor comprising this fluorescent dye.

2. Description of the Related Art

The determination of the H+ activity in aqueous media, i.e. the measurement of the pH, using electrochemical sensors, in particular by means of pH glass electrodes, has been known for a long time. Nevertheless, the use of glass electrodes also has disadvantages in several respects, such as, for example, the problem of miniaturization. Particularly for biotechnological applications in which a noninvasive determination of the pH is required, customary electrochemical sensors show their weaknesses.

For this reason, many attempts have been made in recent years to develop optical pH sensors which, on the one hand, give rise to the known advantages of pH glass electrodes and, on the other hand, can also be used for sensitive pH measurements in biotechnological applications.

However, one problem exhibited by early optical pH sensors was that of "leaching", for which reason these sensors were in most cases only able to be used once ("single-use"). Finally, fluorescence-based optical pH sensors have been increasingly described, where a fluorescent dye acts as "indicator". Depending on the pH, such fluorescent dyes have a change in the excitation or emission wavelength. If, for example, the fluorescent dye has two different excitation wavelengths, then the pH can be determined from the quotient of the intensities measured in succession at the two excitation wavelengths ("dual excitation"/"single emission" process). This ratiometric measurement process is a particularly reliable method for determining the pH since it is relatively unsusceptible to disturbance, for example to fluctuations in intensity.

This principle of measuring the pH in aqueous media for biotechnological applications using fluorescence-based optical chemosensory is described for example in U.S. Pat. No. 7,390,462 B2. For this purpose, the fluorescent dyes hydroxypyrenetrisulfonic acid (HPTS) or, in a further embodiment, dihydroxypyrenedisulfonic acid (DHPDS) are immobilized in an analyte-permeable matrix and introduced into containers such as, for example, bioreactors. The sensors are read by means of suitable optoelectronics through the transparent wall of the container in accordance with the aforementioned "dual excitation"/"single-emission" process. For the HPTS-based variant, the fluorescence of the dye at 408 nm and at 468 nm is stimulated by means of suitable LEDs, and the fluorescence emission at 515 nm is measured using a photodiode. The quotient of the intensities measured in succession at the two excitation wavelengths can be used to calculate the pH according to a sigmoidal relationship.

For the DHPDS-based sensors, the maxima of the excitation are at 404 nm and 457 nm; the maximum of the emission is at 502 nm. The two maxima of the excitation for both dyes each correlate with the conjugated acid-base pair of the respective dye.

On account of the excitation of the two dyes in the wavelength range at 404 nm and 408 nm respectively, corresponding optoelectronics are not able to bind onto the sensors via inexpensive POF ("polymer optical fibers"), which consist for example of polymethyl methacrylate (PMMA) (e.g. PGR-FB2000, Toray). At these low wavelengths, the PMMA-POF fluoresce themselves and lead to distortion of the measurement signal.

The measurement range for the HPTS- and the DHPDS-based sensor is given in U.S. Pat. No. 7,390,462 B2 as ca. pH 6-9. This measurement range is generally adequate for biotechnological applications, here specifically the cultivation of mammalian cells.

However, for insect cell cultivations, such as, for example, the cell line SF9, and also unregulated batch cultivations of *Escherichia coli*, as well as cultivations of yeasts, such as, for example, *Pichia pastoris* or *Saccharomyces cerevisiae*, a sensitive pH measurement range in the range from pH 4 to pH 8 is required. For this purpose, the sensors described in U.S. Pat. No. 7,390,462 B2 cannot be used and/or would have to be modified in a complex manner using additional dyes (auxiliary dyes), such as, for example, fluorescein or its derivatives, in order to cover this measurement range.

Moreover, these HPTS- and DHPDS-based sensors have a disadvantage in that the determination of the pH value is heavily influenced by the ionic strength in the medium to be measured. This problem is evident in particular with continuous pH measurements in biotechnological applications in which the electrolyte concentration or the ionic strength can vary considerably in the samples to be tested. If the optical pH sensor is sensitive to a change in ionic strength, there is the risk that the measurement results obtained will be affected by errors.

It is therefore an object of the present invention to provide a fluorescent dye, and also an optical sensor which includes this fluorescent dye, which does not have the aforementioned disadvantages of known optical pH sensors. In particular, it is an object of this invention to provide a fluorescent dye which, compared to conventional fluorescence-based optical pH sensors, permits an extended measurement range, especially shifted to more strongly acidic pH values, without using additional auxiliary dyes. Moreover, this fluorescent dye should be relatively insensitive to changes in ionic strength and at the same time be able to be produced cost-effectively.

SUMMARY OF THE INVENTION

A fluorescent dye with the following formula (I) is provided formula (I)

where X is selected from hydrogen, an unsubstituted or substituted $C_{1-20}$ alkyl group, an unsubstituted or substituted $C_{1-20}$ alkoxy group, an unsubstituted or substituted $C_{1-20}$ alkenyl group, an unsubstituted or substituted $C_{1-20}$ alkynyl group, an unsubstituted or substituted $C_{1-20}$ aryl group and an unsubstituted or substituted $C_{1-20}$ heteroaryl group, where the substituents are selected from the group comprising halogens, hydroxyl, carbonyl, cyano, thionyls, amino groups, amides and carboxyl groups, and salts thereof or combinations thereof.

In a preferred embodiment, the fluorescent dye according to the invention has the following formula (II)

formula (II)

where n is an integer from 1 to 20. Particular preference is given to the fluorescent dye of the formula (II) where n is an integer from 2 to 4. According to the present invention, the repeat units shown in formula (II) that are expressed by n are not limited to linear carbon chains, i.e. the fluorescent dye of the formula (II) according to the invention can have either straight-chain alkyl groups or branched alkyl groups in the corresponding repeat units.

According to this embodiment, the fluorescent dye of the formula (II) according to the invention, where n is an integer from 2 to 4, includes in particular 1,3-bis[N-(3-amino-3-carboxypropyl)sulfamoyl]-6,8-dihydroxypyrene, 1,3-bis[N-(3-amino-3-carboxy-1-methylpropyl)sulfamoyl]-6,8-dihydroxypyrene, 1,3-bis[N-(3-amino-3-carboxy-2-methylpropyl)sulfamoyl]-6,8-dihydroxypyrene, 1,3-bis[N-(4-amino-4-carboxybutyl)sulfamoyl]-6,8-dihydroxypyrene, 1,3-bis[N-(3-amino-3-carboxy-1,1-dimethyl-propyl)sulfamoyl]-6,8-dihydroxypyrene, 1,3-bis[N-(3-amino-3-carboxy-2,2-dimethylpropyl)sulfamoyl]-6,8-dihydroxypyrene, 1,3-bis[N-(3-amino-3-carboxy-1,2-dimethylpropyl)sulfamoyl]-6,8-dihydroxypyrene, 1,3-bis[N-(3-amino-3-carboxy-1-ethyl-propyl)sulfamoyl]-6,8-dihydroxypyrene, 1,3-bis[N-(3-amino-3-carboxy-2-ethylpropyl)sulfamoyl]-6,8-dihydroxypyrene, 1,3-bis[N-(4-amino-4-carboxy-1-methylbutyl)sulfamoyl]-6,8-dihydroxypyrene, 1,3-bis[N-(4-amino-4-carboxy-2-methylbutyl)sulfamoyl]-6,8-dihydroxypyrene, 1,3-bis[N-(4-amino-4-carboxy-3-methylbutyl)sulfamoyl]-6,8-dihydroxypyrene and 1,3-bis[N-(5-amino-5-carboxypentyl)sulfamoyl]-6,8-dihydroxypyrene.

In a further preferred embodiment of the present invention, the fluorescent dye of the formula (II) according to the invention is 1,3-bis[N-(3-amino-3-carboxypropyl)sulfamoyl]-6,8-dihydroxypyrene, depicted by formula (IIa) below, 1,3-bis[N-(4-amino-4-carboxybutyl)sulfamoyl]-6,8-dihydroxypyrene, depicted by formula (IIb) below, and 1,3-bis[N-(5-amino-5-carboxypentyl)sulfamoyl]-6,8-dihydroxypyrene, depicted by formula (IIc) below.

(IIa)

(IIb)

(IIc)

On account of its pyrene basic structure, the fluorescent dye of the formula (I) according to the invention has fluorescent properties which can be further enhanced through suitable selection of X. For example, this effect can be achieved if X includes structural features which have an extensive delocalized π system, such as, for example, polycyclic (hetero)aromatics. In this connection, mention may be made for example of naphthalene, anthracene, phenanthrene and tetracene.

According to the invention, on account of the hydroxyl groups and sulfamoyl groups, the fluorescent dye of the formula (I) has at least two different maxima of the excitation wavelengths or emission wavelengths, each of which corresponds to the conjugated acid-base pair of the fluorescent dye. Consequently, the fluorescent dye of the formula (I) is excited at two different wavelengths, i.e. it has two different maxima in the excitation, or has one excitation wavelength which leads to two different maxima of the fluorescence emission.

In a preferred embodiment, the emission of the fluorescent dye according to the invention is pH-dependent, i.e. the fluorescence intensities change depending on the pH.

In a particularly preferred embodiment, the fluorescent dye of the formula (I) according to the invention has two different maxima of the fluorescence emission, one of these maxima being a pH-dependent intensity maximum, where the two maxima are each above the violet range. In particular, the pH-dependent fluorescence maximum is preferably in a range of >420 nm, particularly preferably in a range of >450 nm, i.e. in the blue range or above.

Consequently, pH-dependent intensity changes in the fluorescence of the fluorescent dye according to the invention can advantageously be monitored in ranges which do not fall within the fluorescence range which is brought about for example by a carrier used or further external influences. Moreover, the fluorescent dye according to the invention permits the use of optoelectronics which can be bound to the sensors via inexpensive polymer optical fibers based on polymethyl methacrylate, such as for example PGR-FB2000, produced by Toray.

Furthermore, according to the present invention, a process for preparing the fluorescent dye with the formula (I) is provided. The process according to the invention involves the steps of:

reacting a compound of the following formula (III) to give a compound of the following formula (IV) and reacting the compound having the formula (IV) with a compound of the formula X-NHR, in order to obtain the fluorescent dye of the formula (I).

Formula (I)

Formulae (III) and (IV):

(III)

(IV)

According to the present invention, X in the formula X-NHR has the same meaning as defined above for the formula (I).

In the formula X-NHR, R is hydrogen or a cationic group. The cationic group is any group which can enter into a reaction with the Lg group defined below and is separated off with the formation of a sulfonamide bond (NH—SO$_2$ bond). By way of example, alkali metal salts may be mentioned.

In the formula (III), M is hydrogen or an alkali metal selected from Li, Na and K. If M in formula (III) is hydrogen, this compound is converted in the process according to the invention preferably firstly into a corresponding salt in order to increase the reactivity of this compound. M in the formula (III) is preferably Na since this Na salt is commercially available, as a result of which any complex synthetic preliminary stages can be dispensed with.

In formula (IV), Pg is a protective group. The protective group is not limited and can be a protective group which is familiar to the person skilled in the art and is customary in particular for hydroxyl groups. For example, the protective group can be a silyl protective group, such as, for example, TMS (trimethylsilyl), TBDMS (t-butyldimethylsilyl), TES (triethylsilyl), TIPS (triisopropylsilyl) or TBDPS (t-butyldiphenylsilyl), an ether-forming protective group, such as, for example, methyl, benzyl, p-methoxybenzyl or trityl (triphenylmethyl), an ester-forming protective group, such as, for example, acetyl, pivaloyl or benzoyl, or a sulfonate-forming protective group, such as, for example, tosyl (p-toluenesulfonate) or methyl (methylsulfonate).

Lg in formula (IV) is a leaving group which is selected from the group consisting of triflate, fluorosulfonate, tosylate, mesylate, chloride, bromide and iodide.

According to the present invention, the reaction of the compound (III) to give the compound of the formula (IV) is not limited. This reaction can take place in one step or over several stages, so-called intermediate stages. For example, in the process according to the invention, firstly the hydroxyl functionalities in compound (III) can be protected and then the sulfonate functionalities can be converted to the function —SO$_2$-Lg in a suitable manner. The reagent for this reaction step is not limited and can be any reagent known to a person skilled in the art with which the leaving group Lg can be introduced into the compound of the formula (III). For example, thionyl chloride can be used for the reaction. In this case, Lg in formula (IV) is for example chloride. Moreover, the person skilled in the art is able to establish the reaction condition suitable in each case, such as, for example, use and selection of a solvent, temperature, pressure and time. Comparable reactions are described in the literature, such as, for example, in AT patent 385 755 or F. E. Cappuccio et al., *J. Fluoresc.* 2004, 14, 521-533.

According to the present invention, the process for the preparation of the fluorescent dye of the formula (I) includes the further step of reacting the compound of the formula (IV) with a compound of the formula X-NHR. This process step is not subject to any limitation. According to the invention, the compound of the formula X-NHR can be an amine. In this case, i.e. R=H, the amine can also be activated beforehand depending on the reactivity of this compound, for example in situ.

In a preferred embodiment, the compound of the formula X-NHR is a diamine with a carboxyl group. According to the present invention, it is particularly preferred that X in this formula is an α-amino acid radical, i.e. this compound has a carboxyl group and an amine group on the same carbon atom. In such cases, a person skilled in the art is able, if necessary, to use suitable protective groups in order to arrive at the compound of the formula (I). For example, if X in the formula X-NHR is an α-amino acid radical, it should be mentioned that the amine functionality in the radical X is protected in a suitable manner.

Of particular suitability for this are known protective groups, such as for example carbamates, such as Boc (t-butyl carbamate), Fmoc (9-fluorenyl-methyl carbamate), benzyl carbamate and allyl carbamate.

If the amine derivative X-NHR has firstly been provided with a suitable protective group, this protective group is removed again after the reaction of this compound with the compound of the formula (IV). In this connection, a person skilled in the art is able to select the reaction conditions depending on the protective group used in such a way as to remove the protective group again.

In a preferred embodiment of the process according to the invention for the preparation of the fluorescent dye (I), the compound X-NHR used in the reaction with the compound of the formula (IV) is a compound of the following formula (V):

Formula (V)

where R is as defined above and n is an integer from 1 to 20, preferably an integer from 2 to 4, and the repeat unit expressed thereby can be straight-chain or branched-chain.

Furthermore, an optical pH sensor comprising the fluorescent dye of the formula (I) according to the invention is provided according to the present invention. In particular, the optical pH sensor according to the invention comprises an analyte-permeable carrier on which the fluorescent dye according to the invention is immobilized.

According to the present invention, the analyte-permeable carrier used is preferably a matrix in which the fluorescent dye according to the invention can be immobilized. In particular, suitable carriers are wet-strength filter papers or a similar cellulose matrix.

In a preferred embodiment, the thickness of the carrier is between 50 μm and 500 μm, particularly preferably between 100 μm and 300 μm. Particular preference is given to carriers which have a thickness of from 100 μm to 200 μm.

According to the present invention, the fluorescent dye of the formula (I) according to the invention is provided or immobilized on the carrier such that it is firmly bonded to the carrier. So-called "leaching" of the fluorescent dye is thereby advantageously avoided. Of particular suitability for this bonding of the fluorescent dye to the carrier is a process in which the carrier is impregnated with a reactive mixture comprising the fluorescent dye according to the invention.

According to the present invention, the preparation of the pH sensor according to the invention, and how the fluorescent dye according to the invention is immobilized on the carrier, is not subject to any limitation. In this connection, the reactive mixture can comprise the fluorescent dye according to the invention, which is optionally firstly activated, and further constituents which enable it for example to immobilize the reactive mixture in the form of a hydrogel on the carrier.

DETAILED DESCRIPTION

Figure 1:
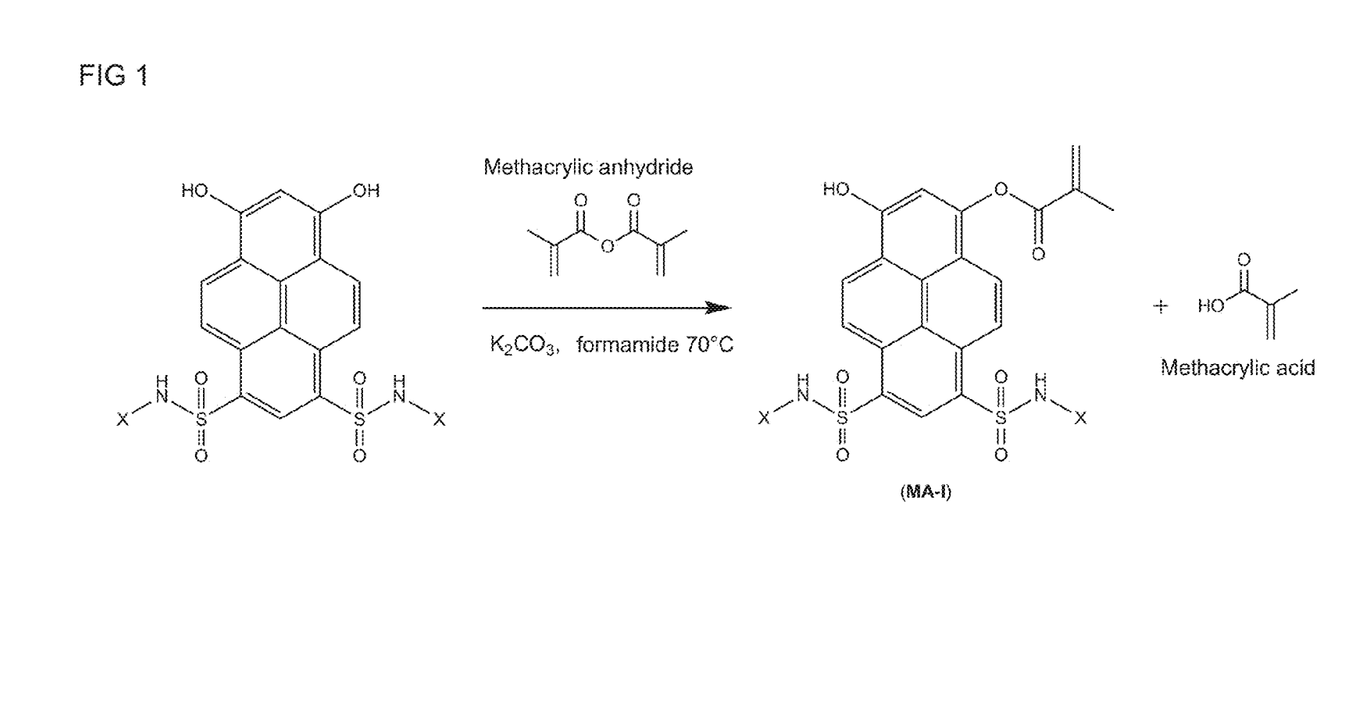
FIG. 1 schematically illustrates a reaction of the fluorescent dye of the invention with methacrylic anhydride to give the corresponding monomethacrylate derivative.

For example, the fluorescent dye according to the invention can be present in a reactive mixture comprising polymerizable monomer units with which the carrier is firstly impregnated, and these are then immobilized by polymerization on the carrier in a suitable manner. Suitable polymerizable monomer units are for example polymerizable monomers based on (meth)acrylic acid. The fluorescent dye according to the invention can for example be immobilized on the carrier analogously to the process described in U.S. Pat. No. 7,390,462 B2. As shown in FIG. 1, the fluorescent dye according to the invention can be reacted with methacrylic anhydride to give the corresponding monomethacrylate derivative. This monomethacrylate derivative of the fluorescent dye MA-I according to the invention can be impregnated for example together with polyethylene glycol dimethacrylate (PEG dimethacrylate) as reactive mixture on the carrier and be immobilized by subsequent polymerization on the carrier (cf. FIG. 2). In particular, besides the polymerizable monomer units discussed and the derivative of the fluorescent dye according to the invention MA-I, the reactive mixture can comprise further additives which influence the polymerization in a suitable manner.

Figure 2:
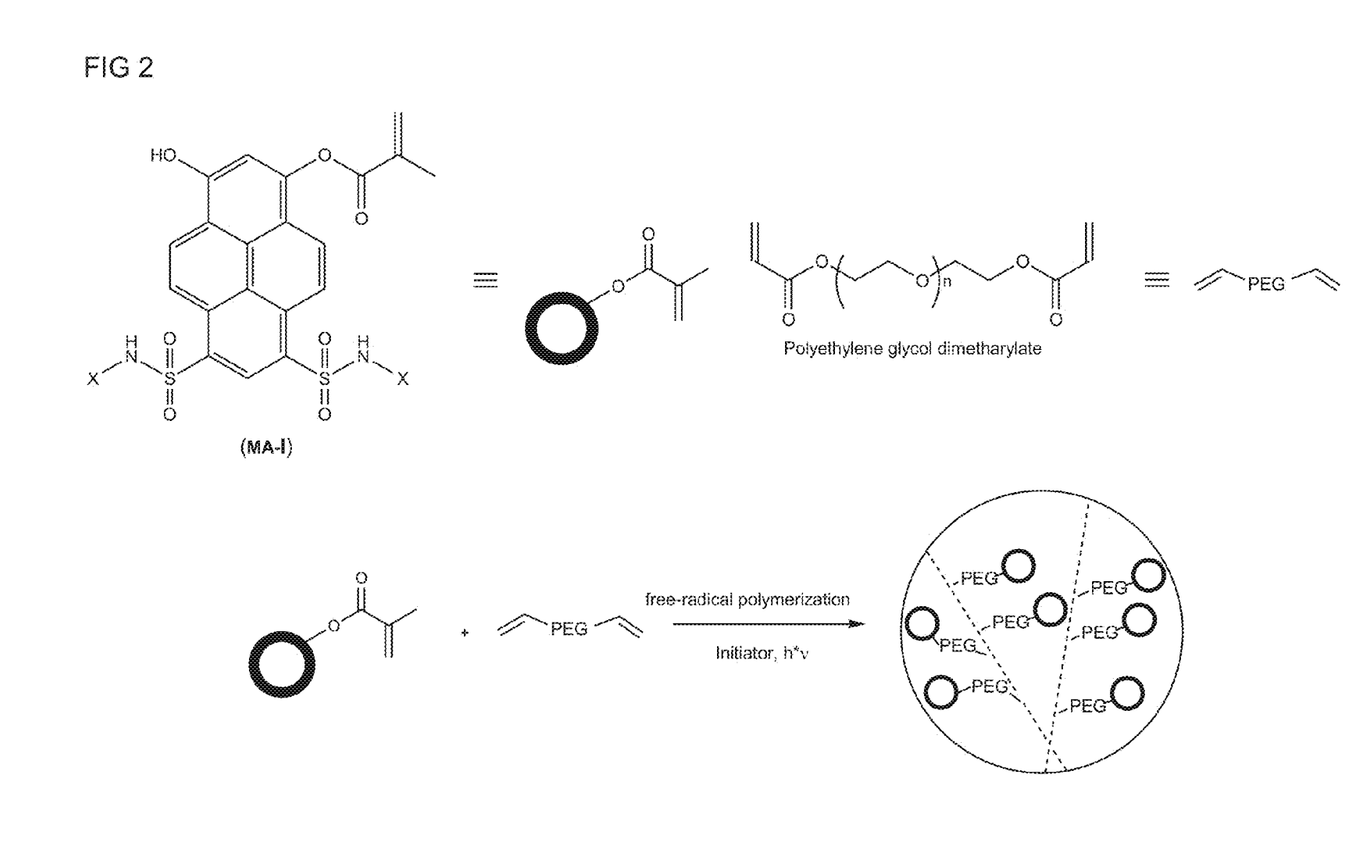
FIG. 2 schematically illustrates the reactive mixture comprising the derivative of the fluorescent dye of the invention MA-I, PEG dimethacrylate and a suitable photoinitiator immobilized on the carrier by polymerization.

In particular, the reactive mixture can also comprise a polymerization inhibitor which, initiated thermally and/or photochemically, can start a free-radical polymerization. As shown in FIG. 2, the reactive mixture comprising the derivative of the fluorescent dye according to the invention MA-I, PEG dimethacrylate and a suitable photoinitiator can be immobilized on the carrier by polymerization.

For example, the optical pH sensor according to the invention can be produced by free-radical polymerization of a reactive mixture which comprises 1,3-bis[N-(5-amino-5-carboxypentyl)sulfamoyl]-6,8-dihydroxypyrene methacrylate, iso-propanol, 50 mM phosphate buffer (pH 7.0, ionic strength 150 mM), PEG-400 dimethacrylate, and also the photoinitiator Darocur®. A wet-strength filter paper of thickness 150 µm is impregnated with the reactive mixture and irradiated every 60 seconds from both sides with UV light (5 mW/cm$^2$, 360 nm). The impregnated matrix is then boiled twice in ultrapure water for 20 min in order to wash out unpolymerized constituents of the reactive mixture, and then dried at 70° C. for 24 hours.

According to a preferred embodiment of the present invention, the optical pH sensor also comprises at least one coating which is provided on at least one of the two surfaces of the carrier on which the fluorescent dye according to the invention is immobilized. According to the invention, the pH sensor more advantageously comprises a coating on both surfaces of the carrier, as a result of which the pH sensor can be protected for example particularly effectively against external damage.

This coating can be a coating which is known to the person skilled in the art and is preferably transparent. Of particular suitability are coatings made of glass or plastics. According to the invention, for example plastic films can be laminated onto the carrier. By way of example, mention may be made of a PET-PE laminating film which consists of a 40 µm-thick polyethylene terephthalate layer (PET) and an 8 µm-thick polyethylene layer (PE). This laminating film can for example be applied by hot lamination at 135° C.

According to the invention, the pH sensor with a coating moreover advantageously permits the preparation of for example an adhesive layer on the coating, as a result of which the pH sensor according to the invention can for example be fixed to a container in which the medium to be tested and/or monitored as regards the pH is provided. In this case, the pH sensor according to the invention can be read by means of suitable optoelectronics through a transparent wall from the reverse side.

Figure 3:
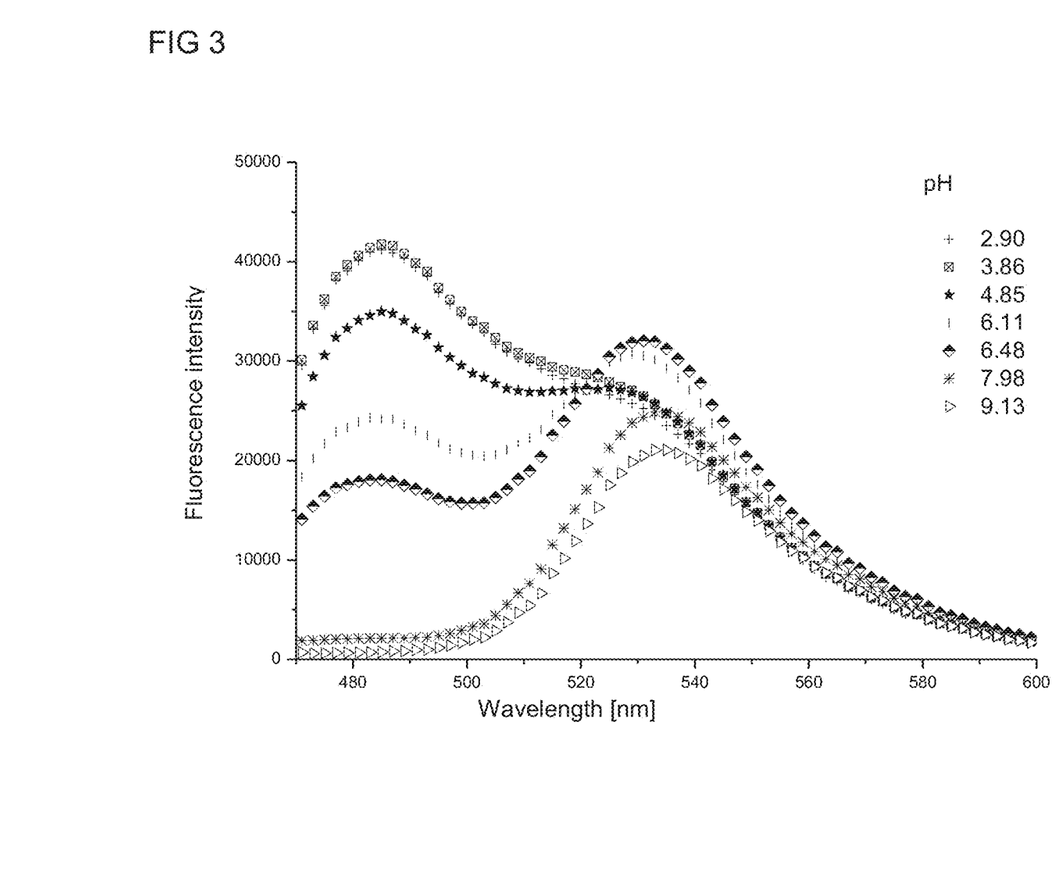
FIG. 3 shows fluorescence spectra of an optical pH sensor according to the invention, comprising 1,3-bis[N-(5-amino-5-carboxypentyl)sulfamoyl]-6,8-dihydroxypyrene (IIc) as fluorescent dye.
Figure 4:
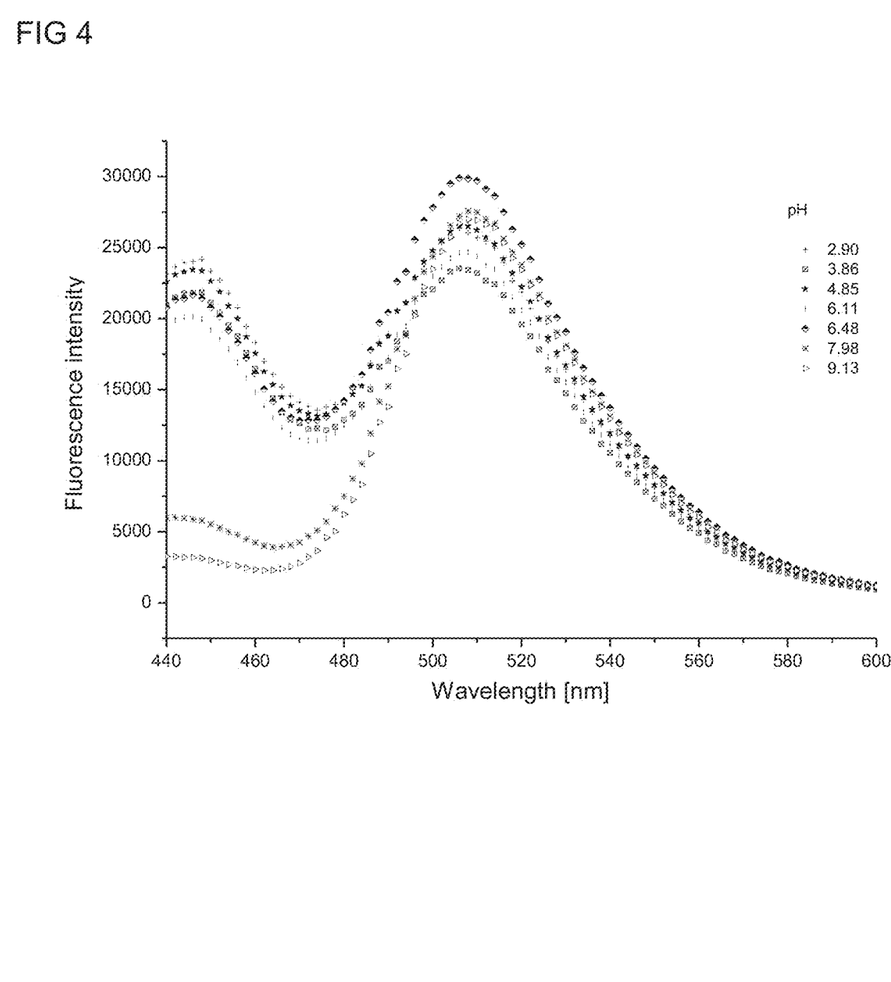
FIG. 4 shows fluorescence spectra of a sensor described in U.S. Pat. No. 7,390,462 B2 and prepared with DHPDS, which was tested under the same conditions.

FIG. 3 shows fluorescence spectra of an optical pH sensor according to the invention, comprising 1,3-bis[N-(5-amino-5-carboxypentyl)sulfamoyl]-6,8-dihydroxypyrene (IIc) as fluorescent dye. The spectra were recorded using a Tecan laboratory spectrofluorometer (excitation at 445 nm). For this purpose, 4 mm round blanks of the sensor material were covered, in a black 96-well plate (Corning) having a transparent base, with 50 mM buffer of ionic strength 150 mM (adjusted with NaCl) and pH values of from pH 2.9 to pH 9.13 and left to swell for 1 hour. The subsequent measurement was carried out at excitation with 445 nm (corresponds to the maximum of the excitation spectrum during fluorescence measurement at 530 nm) with a resolution of 4 nm. The fluorescence maximum at 485 nm correlates with the pH, i.e. as the pH value decreases, an increasing fluorescence intensity is detected at 485 nm; the second maximum, which readily shifts in the range between 535 nm and 530 nm depending on pH, exhibits no direct pH dependency and serves as spectral reference for the pH-dependent maximum (cf. FIG. 3). In comparison, FIG. 4 shows fluorescence spectra of a sensor described in U.S. Pat. No. 7,390,462 B2 and prepared with DHPDS, which was tested under the same conditions.

Figure 7:
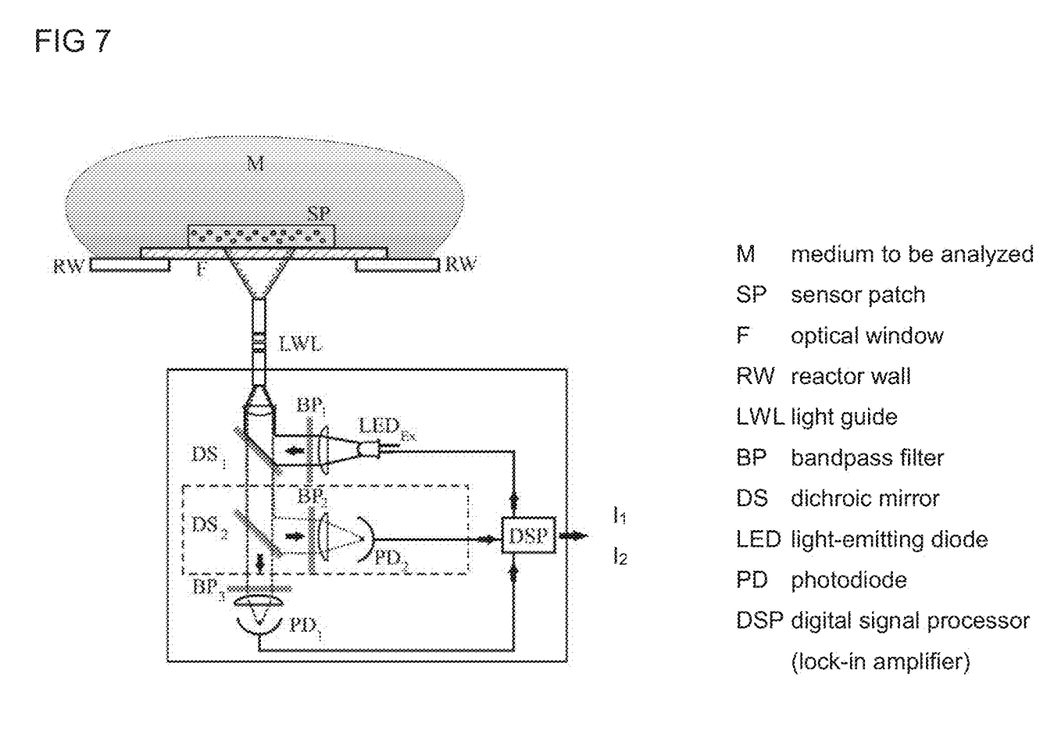
FIG. 7 shows optoelectronics that uses a light-emitting diode to achieve excitation for measuring the fluorescence intensities at two wavelengths (e.g. 485 nm and 530 nm).

By measuring by means of suitable optoelectronics, as shown for example in FIG. 7, the fluorescence intensities at both wavelengths (485 nm and 530 nm) can be determined under excitation by means of a light-emitting diode (445 nm).

By using a ratiometric measurement process, where the resulting intensities I(485 nm) and I(530 nm) are divided in accordance with the "dual excitation"/"single emission" process, a measurement process can be provided that is robust and unsusceptible to disturbance, particularly as regards fluctuations in intensity.

Figure 6:
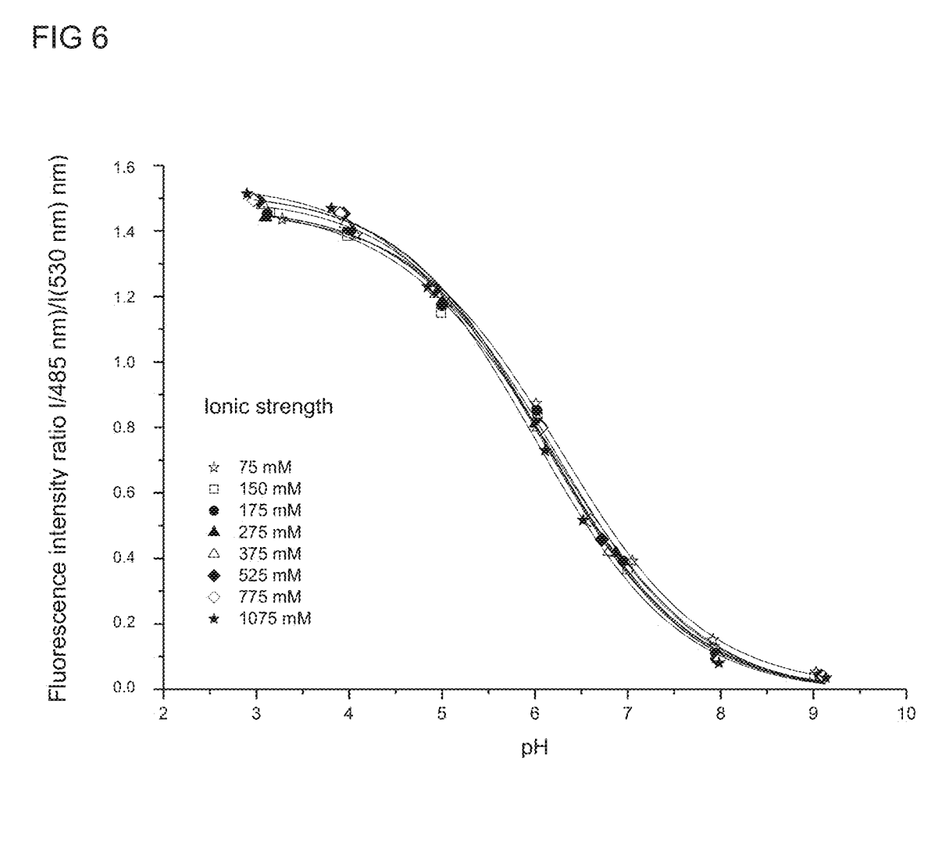
FIG. 6 shows curves in which the resulting intensity quotients are plotted against the pH, the pH values having been measured in the range from pH 2.9 to pH 9.1.

FIG. 6 shows curves in which the resulting intensity quotients are plotted against the pH, the pH values having been measured in the range from pH 2.9 to pH 9.1. Moreover, the curves for different ionic strengths of the pH buffers used were measured. Within the tested ionic strength range of 75-1075 mM (mMol/L), there is surprisingly a very high agreement of the sensor characteristics for all tested ionic strengths for the optical pH sensor according to the invention comprising 1,3-bis[N-(5-amino-5-carboxypentyl)sulfamoyl]-6,8-dihydroxypyrene (IIc) as fluorescent dye.

Figure 5:
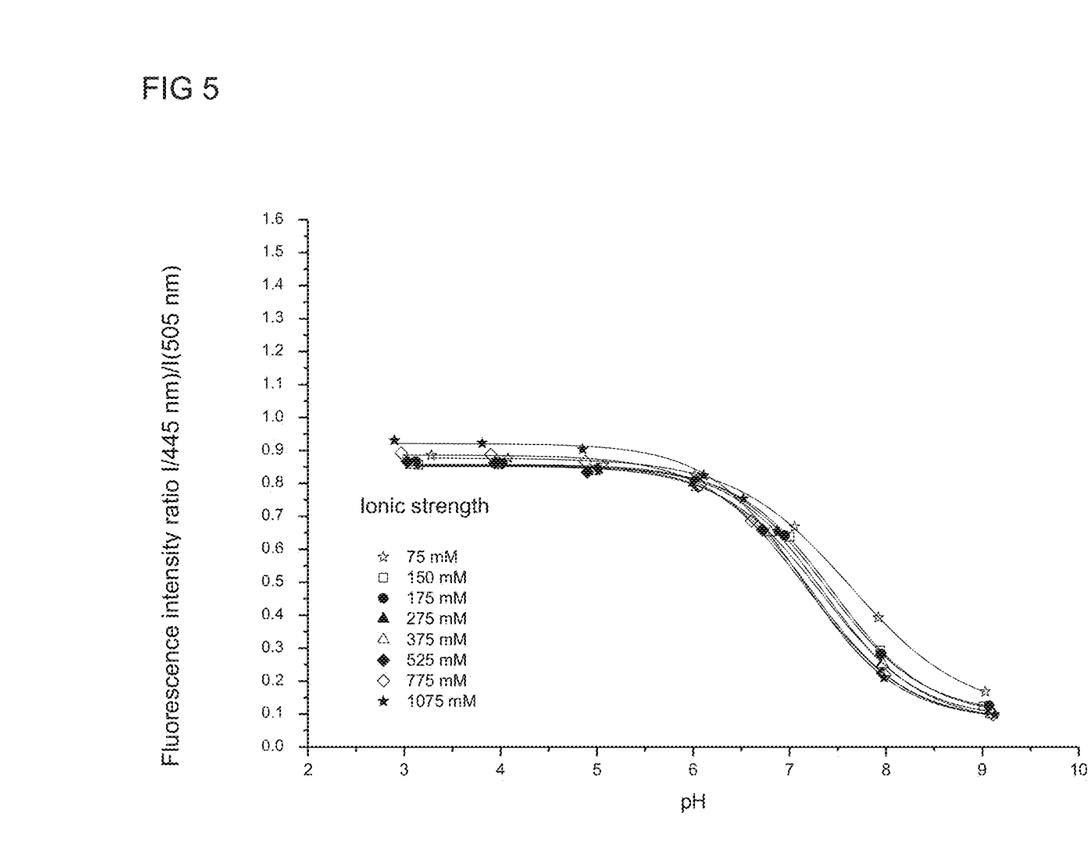
FIG. 5 shows that the characteristic for the sensors produced with DHPDS and described in U.S. Pat. No. 7,390,462 B2 shifts with increasing ionic strength sideways to lower pH values.

Compared to the sensor described in U.S. Pat. No. 7,390,462 B2 and produced with DHPDS, tested under identical conditions, i.e. at an excitation wavelength of 405 nm and with calculation of the intensity quotient I(445 nm)/I(505 nm) (cf. FIG. 5), the pH sensor according to the invention, as shown in FIG. 6, has a very low sensitivity towards the ionic strength. As is evident from FIG. 5, the characteristic for the sensors produced with DHPDS and described in U.S. Pat. No. 7,390,462 B2 shifts with increasing ionic strength sideways to lower pH values, as a result of which the precision of a sensor prepared and precalibrated in this way is impaired. The sensor according to the invention (cf. FIG. 6) does not have such a shift within the scope of measurement accuracy of the Tecan laboratory spectrofluorometer, meaning that more precise measurement values are obtainable for ionic strength that is variable during the measuring operation. This is advantageous particularly when using precalibrated optical pH sensors in regulated fermentations/cell cultivations since the pH regulation, which in most cases is carried out by pumping base into the culture broth which becomes acidic over the course of the cultivation and the cell metabolism, increases the ionic strength. Surprisingly it has been found that the pH sensor according to the invention is not compromised by this increase in ionic strength.

Furthermore, in contrast to the sensor produced with DHPDS and described in U.S. Pat. No. 7,390,462 B2, the pH sensor according to the invention has an extended measurement range shifted to more strongly acidic pH values. The dynamic measurement range of the pH sensor according to the invention with the fluorescent dye IIc corresponds to the linear part of the calibration curve (cf. FIG. 6) and is between pH 4.0 and pH 8.0. On account of the extended dynamic measurement range, the pH sensor according to the invention is also suitable for application in cultivations of organisms which have their pH optimum, i.e. optimum growth and also optimum production rates, in this range. In contrast to this, the dynamic measurement range of the sensor produced with DHPDS lies in the narrower pH range from pH 6.0 to pH 8.5.

By reference to the features explained above and the measurement results, it becomes evident that the new type of fluorescent dye (I) according to the invention as indicator in pH sensors surprisingly leads to an extended measurement range, shifted in particular to more strongly acidic pH values, without additional auxiliary dyes being required. Consequently, the optical pH sensor according to the invention is an effective system which can be produced in a cost-effective manner and can be used over a broad pH range, especially in biotechnological applications. Moreover, compared to comparable known optical pH sensors, the fluorescent dye or optical pH sensor according to the invention has a low sensitivity to changes in ionic strength in the medium to be measured, as a result of which it is significantly easier to carry out the pH determination.

The present invention is explained in more detail by reference to the examples below with regard to the preparation process of the fluorescent dye (I) according to the invention, without being limited thereto.

Examples

General $^1$H-NMR spectra were recorded at 300 MHz using a Varian Mercury Vx300 spectrometer in $CDCl_3$, $D_2O$, $[D_4]$-methanol, $[D_6]$-acetone or $[D_6]$-DMSO. $CHCl_3/CDCl_3$, DHO, $CD_2HOD$, $C_3HD_5O$ and $CD_3SOD_2H$ served as internal reference. ESI-MS and HRMS spectra were recorded using Finnigan-LCQ and Bruker-Daltonic-APEX IV-7T-FTICR instruments respectively. The HPLC analysis was carried out using Synergi MAX-RP C12 as solid phase and MeOH/$H_2O$+0.05% formic acid as eluent. Melting points were ascertained using a Büchi 510 capillary measuring device. All of the chemicals were used in the highest degree of purity commercially available. Anhydrous dichloromethane and THF were prepared using molecular sieve 4 Å in accordance with [D1]. Anhydrous pentane was distilled over sodium. All of the reactions were carried out in the absence of light. Mixtures containing anhydrous solvents were processed in an argon atmosphere in flame-dried glass equipment.

Figure 8:
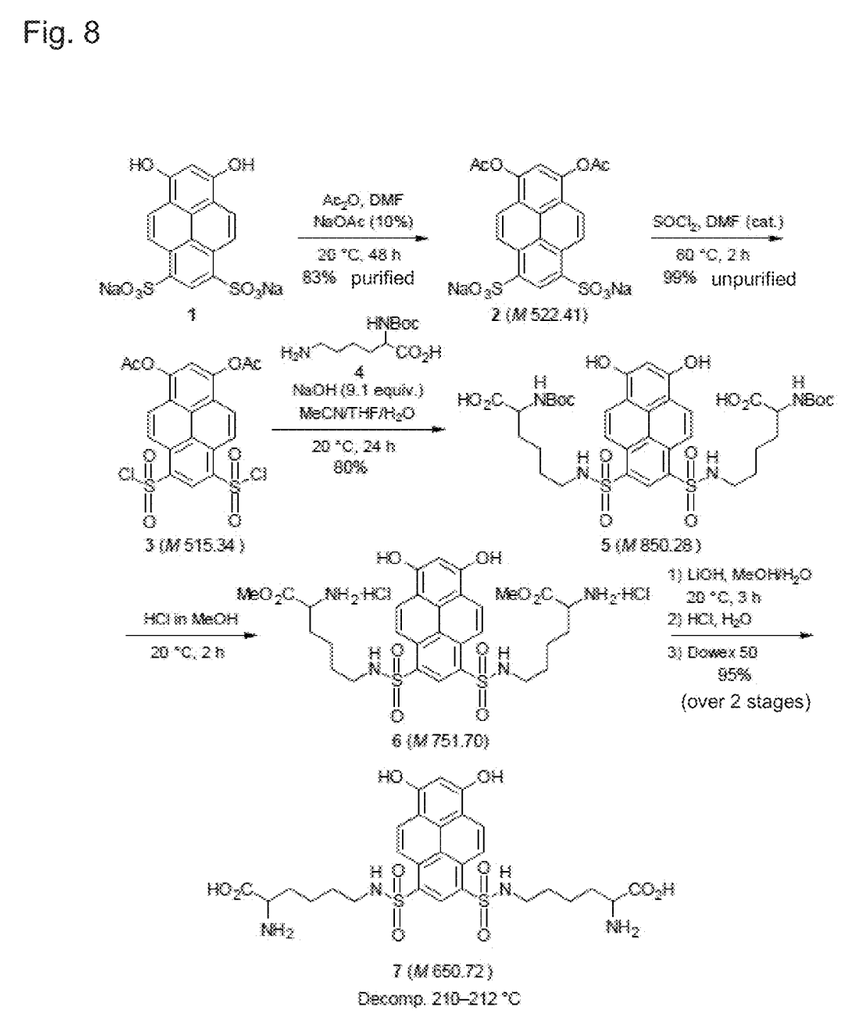
FIG. 8 illustrates the synthesis of 1,3-bis[N-(5-amino-5-carboxypentyl)sulfamoyl]-6,8-dihydroxypyrene IIc (7).

The synthesis of 1,3-bis[N-(5-amino-5-carboxypentyl)-sulfamoyl]-6,8-dihydroxypyrene IIc (7) by the scheme shown in FIG. 8 is described below.

6,8-Diacetoxypyrene-1,3-disulfonic acid sodium salt (2)

Compound (2) was prepared by the protocol already published [D2], but modified here. The modification was that sodium acetate was used [D3]. A mixture of sodium 6,8-dihydroxypyrene-1,3-disulfonate (1) (4.452 g, 10.16 mmol), sodium acetate (83.0 mg, 1.016 mmol) and acetic anhydride (5.8 mL) in DMF (250 mL) was stirred intensively at room temperature for 48 h with the exclusion of light. The reaction mixture was filtered through a Celite-kieselguhr bed (h=0.5 cm), and DMF was stripped off on a rotary evaporator at 50° C. and 0.1 Torr. The residue was recrystallized from an ethanol/water mixture (70 ml:10 ml), washed with acetone and dried in vacuo to give a yield of 4.242 g (83%) as yellow powder (melting point 245-247° C. (decomposition)).

$^1$H NMR (300 MHz, $D_2O$): δ=9.07 (s, 1H), 8.57 (d, J=9.0 Hz, 2H), 7.64 (d, J=9.0 Hz, 2H), 6.90 (s, 1H), 2.30 (s 6H, 2 $CH_3$).

6,8-Diacetoxypyrene-1,3-disulfonyl dichloride (3)

Compound (3) was synthesized in a modification of the protocol given in [D3]. Five drops of DMF were added to the diacetate 2 (5.080 g, 9.724 mmol). 30 ml of thionyl chloride were carefully added to this mixture with stirring and cooling (ice bath). The suspension was refluxed for 2 h, during which the suspension turned brown. After cooling to 25° C. under an argon atmosphere, excess thionyl chloride was distilled off in vacuo. The yellow residue was resuspended in 50 ml of anhydrous dichloromethane and then centrifuged. The supernatant was transferred to a round-bottom flask using a syringe. This process was repeated a further 5 times. The combined supernatants were evaporated to 50 ml under an argon atmosphere. 200 ml of anhydrous pentane were added and, after storage overnight at 4° C., the supernatant was removed. The residue was dried under reduced pressure to constant weight to give a yellow solid (4.962 g, 99%). $^1$H NMR (300 MHz, $CDCl_3$): δ=9.50 (s, 1H), 9.18 (d, J=9.0 Hz, 2H), 8.77 (d, J=9.0 Hz, 2H), 8.14 (s, 1H), 2.62 (s 6H, 2 $CH_3$).

1,3-bis{N-[5-(tert-Butoxycarbonylamino)-5-carboxypentyl]sulfamoyl}-6,8-dihydroxypyrene (5)

The preparation of structurally isomeric derivatives to give (5) has already been published in [D4], but without details relating to the experimental conditions for the preparation of these derivatives. Under an argon atmosphere, Boc-Lys-OH (4) (2.159 g, 8.765 mmol) was dissolved in aqueous 1N sodium hydroxide solution (40 mL), then acetonitrile was added (140 mL), and the reaction mixture was cooled using an ice bath. With energetic stirring, a solution of the dichloride (3) (2.258 g, 4.382 mmol) in anhydrous THF (100 mL) was added dropwise over a period of 3 h at 4° C. The mixture was stirred for a further 21 h at room temperature and then concentrated under reduced pressure. The residue was taken up in water (100 mL), such that an emerald green solution was formed. The solution was titrated with 1N hydrochloric acid to pH 3.5 (ca. ml). The resulting brown precipitate was immediately centrifuged off, washed with water and dried over phosphorus pentoxide overnight to give a brown powder (2.981 g, 80%).

$^1$H NMR (300 MHz, $[D_6]$-acetone): δ=9.19 (s, 1H), 8.76 (d, J=9.0 Hz, 2H), 8.66 (d, J=9.0 Hz, 2H), 7.47 (s, 1H), 6.98 (br. s, 2H, 2 NH), 6.06 (d, J=9.0 Hz, 2H, 2 NH), 4.04 (br. s, 2H, 2 CHN), 2.95 (q, J=6.0 Hz, 4H, 2 $CH_2N$), 1.72-1.40 (m, 12H, 6 $CH_2$), 1.36 (s, 18H, 2 tBu). HRMS (ESI): m/z $[M+Na]^+$ calculated for $C_{38}H_{50}N_4NaO_{14}S_2$ 873.2657; found 873.2659; calculated for $C_{38}H_{50}N_4O_{14}S_2$ 850.2765; found 850.2743.

1,3-bis[N-(5-Amino-5-methoxycarbonylpentyl)sulfamoyl]-6,8-dihydroxypyrene dihydrochloride (6)

60 ml of 10 N HCl in methanol were added at 4° C. to a solution of the bis-Boc derivative 5 (2.673 g, 3.143 mmol) in methanol (80 mL). The reaction mixture was stirred for 10 min at 4° C. and then for a further 2 h at room temperature, then evaporated to dryness under reduced pressure. The residue was dried overnight over phosphorus pentoxide. $^1$H NMR and HRMS (ESI) spectra revealed the formation of the dihydrochloride of the diester 6. Yield 2.340 g (99%). $^1$H NMR (300 MHz, $CD_3OD$): δ=9.10 (s, 1H), 8.69 (d, J=9.0 Hz, 2H), 8.61 (d, J=9.0 Hz, 2H), 7.24 (s, 1H), 3.84-3.79 (m, 2H, 2 CHN), 2.89 (t, J=9.0 Hz, 4H, 2 $CH_2N$), 1.75-1.63 (m, 4H, 2 $CH_2$), 1.47-1.25 (m, 8H, 4 $CH_2$). HRMS (ESI): m/z [M+H] calculated for $C_{30}H_{39}N_4O_{10}S_2$ 679.2108; 679.2102 was found.

1,3-bis[N-(5-Amino-5-carboxypentyl)sulfamoyl]-6,8-dihydroxypyrene (7)

A solution of $LiOH \cdot H_2O$ (1.319 g, 31.43 mmol) in water (20 mL) was added to a solution of the dihydrochloride 6 (2.443 g, 3.250 mmol) in methanol (80 mL). The mixture was stirred vigorously at room temperature for 3 h and then concentrated by evaporation. The residue was taken up in 80 ml of water and 4 ml of conc. hydrochloric acid were added. The reaction mixture was concentrated by evaporation once again and then taken up in 100 ml of water, added to a 4 cm×40 cm column packed with acidic Dowex 50WX2-200, washed with 1.5 L of water and then eluted with 1.5 L of 1N ammonia solution. The emerald green solution of 7, which was evaporated under reduced pressure at 50° C., was dried over phosphorus pentoxide overnight to give the dark brown powder 7 (2.0350 g, 96%). The powder was stirred in 20 ml of water at 70° C. for 20 min, cooled and centrifuged. The sediment was stirred in ice-cold water, centrifuged off and dried overnight over phosphorus pentoxide (1.1907 g). Melting point: 210-212° C. (decomposition). $^1$H NMR (300 MHz, [D$_6$]-DMSO): δ=8.84 (s, 1H), 8.53 (d, J=9.0 Hz, 2H), 8.46 (d, J=9.0 Hz, 2H), 8.15 (br. s, 2H, 2 NH), 7.27 (s, 1H), 3.12 (m, 2H, 2 CHN; overlapping with HOD and NH$_2$), 2.65 (t, J=7.5 Hz, 4H, 2 CH$_2$N), 1.57-1.35 (m, 4H, 2 CH$_2$), 1.30-1.00 (m, 8H, 4 CH$_2$). HRMS (ESI): m/z [M+Na]$^+$ calculated for C$_{28}$H$_{34}$N$_4$NaO$_{10}$S$_2$ 673.1614; found 673.1609; m/z [M−H]$^+$ calculated for C$_{28}$H$_{33}$N$_4$O$_{10}$S$_2$ 649.1638; found 649.1644.

Figure 9:
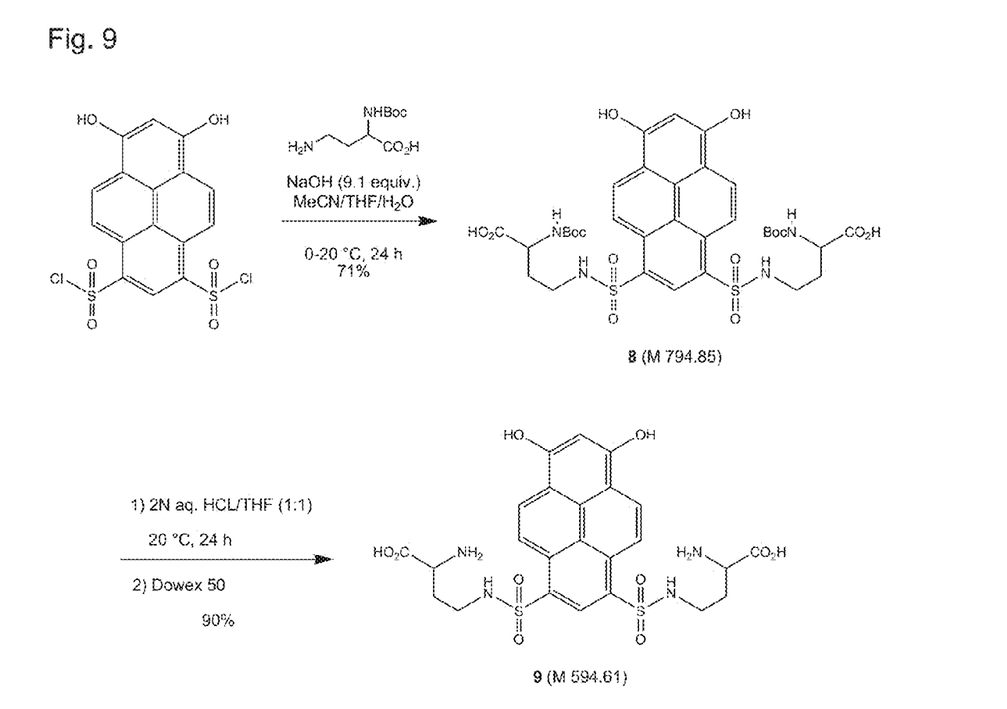
FIG. 9 illustrates the synthesis of 1,3-bis[N-(3-amino-3-carboxypropyl)sulfamoyl]-6,8-dihydroxypyrene (9).

The synthesis of 1,3-bis[N-(3-amino-3-carboxypropyl)-sulfamoyl]-6,8-dihydroxypyrene (9) by the scheme shown in FIG. 9 is described below.

1,3-bis{N-[3-(tert-Butoxycarbonylamino)-3-carboxypropyl]-sulfamoyl}-6,8-dihydroxypyrene (8)

Under an argon atmosphere, L-Boc-Dab-OH (1.288 g, 5.90 mmol) was dissolved in aqueous 1N sodium hydroxide solution (30 mL), then acetonitrile was added (100 mL), and the reaction mixture was cooled using an ice bath. With energetic stirring, a solution of the dichloride (3) (1.520 g, 2.950 mmol) in anhydrous THF (65 mL) was added dropwise over a period of 3 h at 4° C. The mixture was stirred for a further 21 h at room temperature and then concentrated under reduced pressure. The residue was taken up in water (100 mL), such that an emerald green solution was formed. The solution was titrated with 1N hydrochloric acid to pH 3.5 (ca. 19.5 ml). The resulting brown precipitate was centrifuged off immediately, washed with cold water (50 ml), centrifuged again and dried over phosphorus pentoxide overnight to give a brown powder (1.659 g, 71%).

$^1$H NMR (300 MHz, [D$_6$]-acetone): δ=9.21 (s, 1H), 8.75 (d, J=9.0 Hz, 2H), 8.67 (d, J=9.0 Hz, 2H), 7.49 (s, 1H), 7.09 (br. s, 2H, 2 NH), 6.16 (d, J=9.0 Hz, 2H, 2 NH), 4.18 (m, 2H, 2 CHN), 3.06 (m, 4H, 2 CH$_2$N), 2.07-1.75 (dm, 4H, 2 CH$_2$), 1.29 (s, 18H, 2 tBu). HRMS (ESI): m/z [M+Na]$^+$ calculated for C$_{34}$H$_{42}$N$_4$NaO$_{14}$S$_2$ 817.2037; found 817.2059; calculated for C$_{34}$H$_{42}$N$_4$O$_{14}$S$_2$ 794.2139; found 794.2143.

1,3-bis[N-(3-Amino-3-carboxypropyl)sulfamoyl]-6,8-dihydroxypyrene (9)

A 2 N aqueous solution of HCl was added in one portion to a solution of the bis-Boc derivative (8) synthesized above (1.658 g, 2.09 mmol) in THF (200 mL) and the mixture was stirred for 24 h at room temperature. The mixture was then evaporated to dryness under reduced pressure.

$^1$H NMR (300 MHz, D$_2$O): δ=8.27 (s, 1H), 7.15 (d, J=9.0 Hz, 2H), 6.96 (d, J=9.0 Hz, 2H), 5.83 (s, 1H), 4.18 (t, J=9.0 Hz, 2H, 2 CHN), 2.81 (t, J=9.0 Hz, 4H, 2 CH$_2$N), 1.85 (m, 4H, 2 CH$_2$).

The residue was taken up in 80 ml of water and applied to a 4 cm×40 cm column packed with acidic Dowex 50WX2-200, washed with 1.5 L of water and then eluted with 1.5 L of 1N ammonia solution. The emerald green solution, which was evaporated under reduced pressure at 50° C., was dried over phosphorus pentoxide overnight and obtained as a black-brown powder (1.113 g, 90%). Purity >95% (HPLC-MS). $^1$H NMR (300 MHz, [D$_6$]-DMSO): δ=9.0-8.0 (br. s, 8H overlapping with HO, NH and NH$_2$), 8.84 (s, 1H), 8.55 (d, J=9.0 Hz, 2H), 8.46 (d, J=9.0 Hz, 2H), 7.29 (s, 1H), 3.07 (m, 2H, 2CHN), 2.87 (m, 4H, 2 CH$_2$N), 1.74 (m, 4H, 2 CH$_2$). HPLC-MS (ESI): m/z [M+H]$^+$ calculated for C$_{24}$H$_{27}$N$_4$O$_{10}$S$_2$ 595.1. found 595.1. HRMS (ESI): m/z [M+Na]$^+$ calculated for C$_{24}$H$_{26}$N$_4$NaO$_{10}$S$_2$ 617.0988. found 617.0100.

The invention claimed is:

1. A fluorescent dye with the following formula:

where n is an integer from 1 to 20 and the repeat units expressed thereby may be straight-chain or branched-chain.

2. The fluorescent dye of claim 1, where n is an integer from 2 to 4.

3. The fluorescent dye of claim 1, where the fluorescent dye has two different maxima in the fluorescence emission.

4. The fluorescent dye of claim 3, where at least one of the two different maxima in the fluorescence emission has a pH-dependent intensity maximum.

5. The fluorescent dye of claim 4, where the pH-dependent fluorescent maximum is in a range of >420 nm.

6. A process for the preparation of a fluorescent dye of claim 1, comprising:
preparing compound (IV) from compound (III) by the following reaction scheme:

wherein M is selected from the group consisting of hydrogen, Li, Na and K,

Pg is a protective group and

Lg is selected from the group consisting of triflate, fluorosulfonate, tosylate, mesylate, chloride, bromide and iodide; and then preparing the fluorescent dye of claim 2 from compound (IV) by the following reaction scheme:

wherein R is selected from hydrogen or a cationic group; and n is an integer from 1 to 20 and the repeat units expressed thereby may be straight-chain or branched-chain.

7. The process of claim 6, wherein M is sodium.

8. The process of claim 6, where the compound X-NHR used in the reaction with the compound of the formula (IV) has the formula:

where n is an integer from 1 to 20 and the repeat unit expressed thereby may be straight-chain or branched-chain.

9. An optical pH sensor, comprising an analyte-permeable carrier and the fluorescent dye of claim 1 immobilized on the carrier.

10. The optical pH sensor of claim 9, where the carrier has a thickness of 50 μm to 500 μm.

11. The optical pH sensor of claim 9, further comprising at least one coating which is provided on at least one surface of the carrier on which the fluorescent dye is immobilized.

12. The optical pH sensor of claim 11, where the coating is transparent.

13. The optical pH sensor of claim 11, further comprising an adhesive layer on the coating.

14. The optical pH sensor claim 9, wherein the pH sensor has a dynamic measurement range between pH 4.0 to pH 8.0.

\* \* \* \* \*